United States Patent
Claus

(10) Patent No.: US 9,613,440 B2
(45) Date of Patent: Apr. 4, 2017

(54) DIGITAL BREAST TOMOSYNTHESIS RECONSTRUCTION USING ADAPTIVE VOXEL GRID

(71) Applicant: General Electric Company, Schenectady, NY (US)

(72) Inventor: Bernhard Erich Hermann Claus, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 503 days.

(21) Appl. No.: 14/178,702

(22) Filed: Feb. 12, 2014

(65) Prior Publication Data

US 2015/0228092 A1    Aug. 13, 2015

(51) Int. Cl.
| | | |
|---|---|---|
| G06K 9/00 | (2006.01) |
| G06T 11/00 | (2006.01) |
| G06T 5/00 | (2006.01) |
| G06T 5/50 | (2006.01) |
| G06T 7/00 | (2017.01) |
| A61B 6/02 | (2006.01) |
| A61B 6/00 | (2006.01) |

(52) U.S. Cl.
CPC ............ *G06T 11/006* (2013.01); *A61B 6/025* (2013.01); *A61B 6/5205* (2013.01); *G06T 5/003* (2013.01); *G06T 5/50* (2013.01); *G06T 7/003* (2013.01); *A61B 6/502* (2013.01); *A61B 6/54* (2013.01); *G06T 2207/10112* (2013.01); *G06T 2207/20021* (2013.01); *G06T 2207/30068* (2013.01); *G06T 2211/424* (2013.01); *G06T 2211/436* (2013.01)

(58) Field of Classification Search
None
See application file for complete search history.

(56) References Cited

U.S. PATENT DOCUMENTS

| | | | |
|---|---|---|---|
| 6,292,530 B1 * | 9/2001 | Yavus | A61B 6/025 378/22 |
| 6,904,121 B2 | 6/2005 | Claus et al. | |
| 6,950,492 B2 | 9/2005 | Besson | |
| 8,605,975 B2 | 12/2013 | Pan et al. | |
| 2004/0264636 A1 * | 12/2004 | Claus | A61B 6/025 378/26 |
| 2006/0002509 A1 | 1/2006 | Claus et al. | |
| 2007/0036418 A1 | 2/2007 | Pan et al. | |

(Continued)

FOREIGN PATENT DOCUMENTS

| | | |
|---|---|---|
| WO | 2013/011031 A1 | 1/2013 |
| WO | 2013/123091 A1 | 8/2013 |

OTHER PUBLICATIONS

Wu, Gang et al., "Breast Tomosynthesis Reconstruction Using a Grid of Blobs with Projection Matrices", Proceeding IWDM'10 Proceedings of the 10th International Conference on Digital Mammography, 2010, (pp. 243-250, 8 pages total).

*Primary Examiner* — Jason Heidemann
(74) *Attorney, Agent, or Firm* — Melissa K. Dobson

(57) ABSTRACT

Some embodiments are associated with generation of a volumetric image representing an imaged object associated with a patient. According to some embodiments, tomosynthesis projection data may be acquired. A computer processor may then automatically generate the volumetric image based on the acquired tomosynthesis projection data. Moreover, distances between voxels in the volumetric image may be spatially varied.

20 Claims, 14 Drawing Sheets

(56) References Cited

U.S. PATENT DOCUMENTS

| | | | |
|---|---|---|---|
| 2008/0130979 A1* | 6/2008 | Ren | G06T 3/0006 |
| | | | 382/132 |
| 2009/0207969 A1* | 8/2009 | Fischer | A61B 6/502 |
| | | | 378/37 |
| 2010/0135558 A1* | 6/2010 | Ruth | G06T 11/006 |
| | | | 382/131 |
| 2012/0014501 A1 | 1/2012 | Pelc et al. | |
| 2012/0195484 A1 | 8/2012 | Ren et al. | |

\* cited by examiner

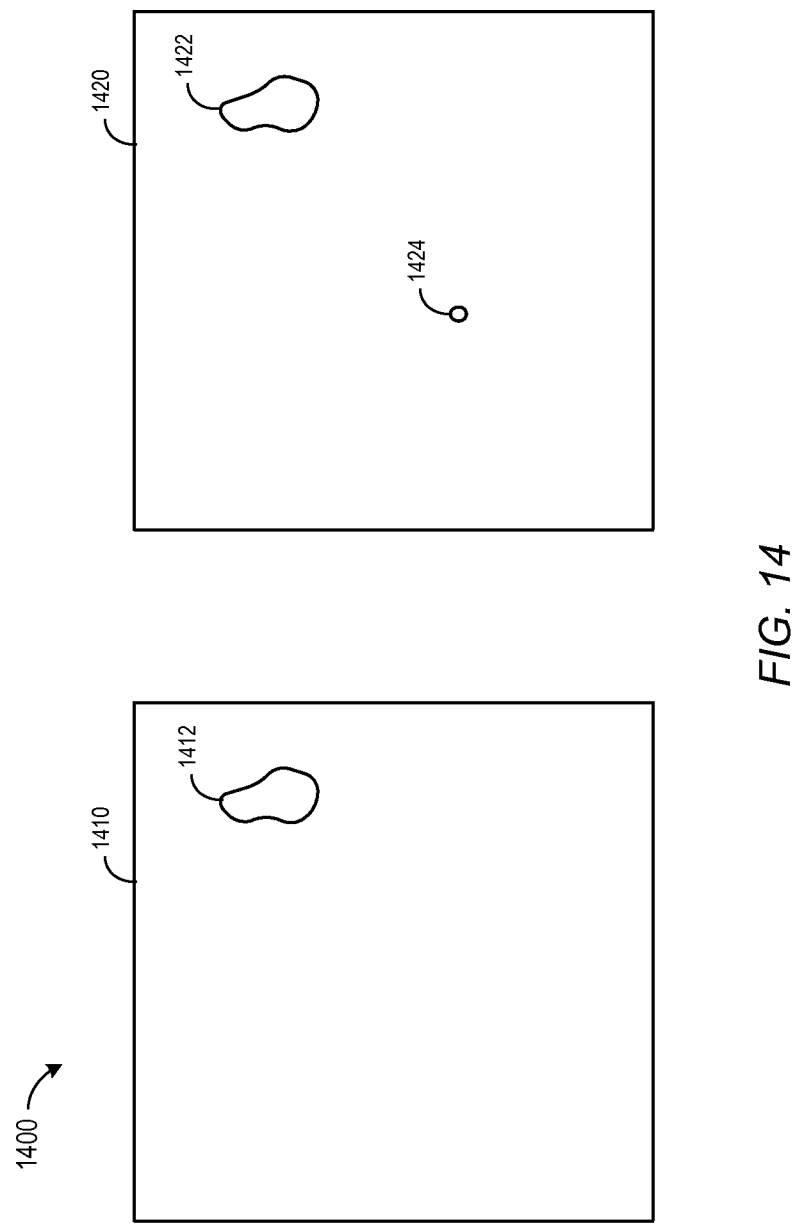

DIGITAL BREAST TOMOSYNTHESIS RECONSTRUCTION USING ADAPTIVE VOXEL GRID

BACKGROUND

The invention relates generally to tomographic imaging and, more particularly, to methods and systems for automatically generating a volumetric image using an adaptive voxel grid.

Tomographic imaging has become an integral part of healthcare services, allowing physicians and radiologists to obtain three-dimensional representations of selected organs or tissues of a patient non-invasively. Tomosynthesis is a variation of conventional planar tomography in which a limited number of radiographic projections are acquired at different angles relative to the patient. In tomosynthesis, an X-ray source produces a fan or cone-shaped X-ray beam that is collimated and passes through the patient to then be detected by a set of detector elements. The detector elements produce a signal based on the attenuation of the X-ray beams. The signals may be processed to produce a radiographic projection, including generally the line integrals of the attenuation coefficients of the object along the ray path. The source, the patient, or the detector are then moved relative to one another for the next exposure, typically by moving the X-ray source, so that each projection is acquired at a different angle.

By using reconstruction techniques, such as filtered back-projection, the set of acquired projections may then be reconstructed to produce diagnostically useful three-dimensional images. Because the three-dimensional information is obtained digitally during tomosynthesis, the image can be reconstructed in whatever viewing plane the operator selects. Typically, a set of slices representative of some volume of interest of the imaged object is reconstructed, where each slice is a reconstructed image representative of structures in a plane that is essentially parallel to the detector plane, and each slice corresponds to a different distance of the plane from the detector plane.

In Digital Breast Tomosynthesis ("DBT"), volume datasets are typically reconstructed with an anisotropic voxel size, where the in-plane voxel spacing within a slice usually reflects the detector pixel size (e.g., 0.1 mm), and the slice separation is generally between 0.5 and 1.0 millimeter (mm). This anisotropic voxel spacing results from a combination of the limited angular range acquisition, workflow considerations (image review time), and data storage considerations. When the overall tomographic angle is increased, slice spacing may need to be reduced to avoid losing (or degrading) fine-scale image detail (e.g., small microcalcifications). That is, a blurring effect and an associated loss in contrast for small microcalcifications may result in a reduced sensitivity of tomosynthesis for the detection of microcalcifications as compared to standard Full Field Digital Mammography ("FFDM") unless slices with a finer slice spacing are provided. It may be impractical, however, to reduce slice spacing in view of workflow and/or data storage considerations.

It would therefore be desirable to reconstruct a tomosynthesis image in such a way so as to improve image quality (e.g., with respect to small microcalcifications).

BRIEF DESCRIPTION

According to some embodiments, tomosynthesis projection data may be acquired. A volumetric image may then be generated based on the acquired tomosynthesis projection data, where distances between voxels in the volumetric image may be spatially varying, i.e., the voxel spacing in some locations of the volume may be different from the voxel spacing in some other locations within the volume. The volumetric image may then be stored in a data storage system and/or displayed on a display system.

Other embodiments are associated with systems and/or computer-readable medium storing instructions to perform any of the methods described herein.

DRAWINGS

FIG. 14 is an example of results that may be achieved according to some embodiments described herein.

DETAILED DESCRIPTION

Embodiments disclosed herein include an imaging method to reconstruct a tomosynthesis image in such a way so as to improve image quality (e.g., with respect to small microcalcifications). Some embodiments are associated with systems and/or computer-readable medium that may help perform such a method.

Figure 1:
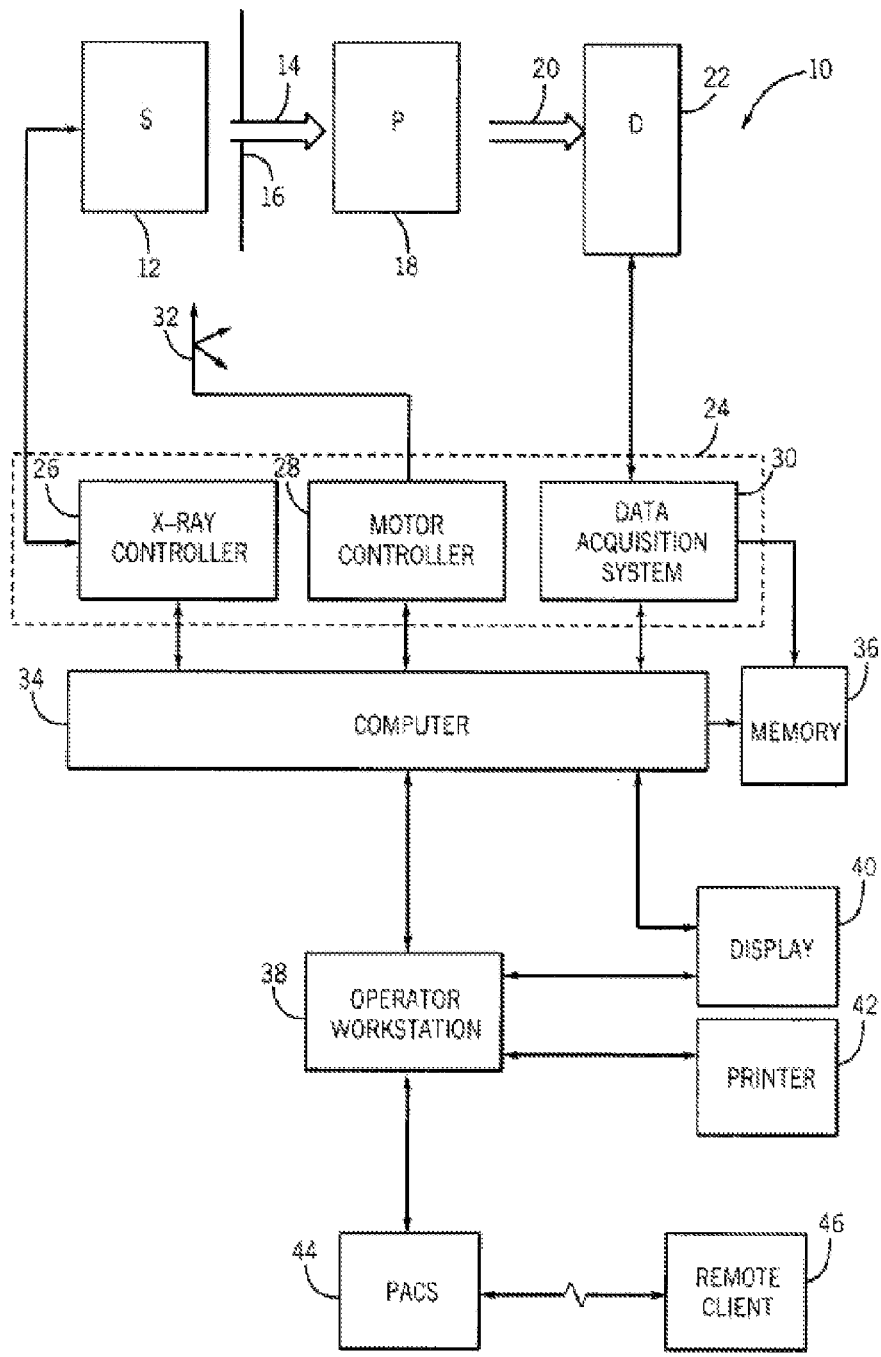
FIG. 1 is a diagrammatical view of an exemplary imaging system in the form of a tomosynthesis imaging system for use in producing processed images in accordance with aspect of some embodiments.

FIG. 1 is a diagrammatical representation of an exemplary tomosynthesis system, designated generally by the reference numeral 10, for acquiring, processing and displaying tomosynthesis images, including images of various slices or slabs through a subject of interest in accordance with the present techniques. In the embodiment illustrated in FIG. 1, the tomosynthesis system 10 includes a source 12 of X-ray radiation which is movable generally in a plane, or in three dimensions. In the exemplary embodiment, the X-ray source 12 typically includes an X-ray tube and associated support and filtering components.

A stream of radiation 14 is emitted by source 12 and passes into a region of a subject, such as a human patient 18. A collimator 16 serves to define the size and shape of the X-ray beam 14 that emerges from the X-ray source toward the subject. A portion of the radiation 20 passes through and around the subject, and impacts a detector array, represented generally by reference numeral 22. Detector elements of the array produce electrical signals that represent the intensity of the incident X-ray beam. These signals are acquired and processed to reconstruct an image of the features within the subject.

Source 12 is controlled by a system controller 24 which furnishes both power and control signals for tomosynthesis examination sequences, including position of the source 12 relative to the subject 18 and detector 22. Moreover, detector 22 is coupled to the system controller 24 which commands acquisition of the signals generated by the detector 22. The system controller 24 may also execute various signal processing and filtration functions, such as for initial adjustment of dynamic ranges, interleaving of digital image data, and so forth. In general, the system controller 24 commands operation of the imaging system 10 to execute examination protocols and to process acquired data. In the present context, the system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, the system controller 24 includes an X-ray controller 26 which regulates generation of X-rays by the source 12. In particular, the X-ray controller 26 is configured to provide power and timing signals to the X-ray source 12. A motor controller 28 serves to control movement of a positional subsystem 32 that regulates the position and orientation of the source 12 with respect to the subject 18 and detector 22. The positional subsystem may also cause movement of the detector 22, or even the patient 18, rather than or in addition to the source 12. It should be noted that in certain configurations, the positional subsystem 32 may be eliminated, particularly where multiple addressable sources 12 are provided. In such configurations, projections may be attained through the triggering of different sources of X-ray radiation positioned differentially relative to the patient 18 and/or source 22. Finally, in the illustration of FIG. 1, detector 22 is coupled to a data acquisition system 30 that receives data collected by read-out electronics of the detector 22. The data acquisition system 30 typically receives sampled analog signals from the detector and converts the signals to digital signals for subsequent processing by a computer 34. Such conversion, and indeed any preprocessing, may actually be performed to some degree within the detector assembly itself.

The computer 34 is typically coupled to the system controller 24. Data collected by the data acquisition system 30 is transmitted to the computer 34 and, moreover, to a memory device 36. Any suitable type of memory device, and indeed of a computer, may be adapted to the present techniques, particularly processors and memory devices adapted to process and store large amounts of data produced by the system 10. Moreover, the computer 34 may be configured to receive commands and scanning parameters from an operator via an operator workstation 38, typically equipped with a keyboard, mouse, or other input devices. An operator may control the system via these devices, and launch examinations for acquiring image data. Moreover, the computer 34 is adapted to perform reconstruction of the image data as discussed in greater detail below. Where desired, other computers or workstations may perform some or all of the functions of the present technique, including post-processing of image data accessed from memory device 36 or another memory device at the imaging system location or remote from that location.

In the diagrammatical illustration of FIG. 1, a display 40 is coupled to the operator workstation 38 for viewing reconstructed images and for controlling imaging. Additionally, the images may also be printed or otherwise output in a hardcopy form via a printer 42. The operator workstation, and indeed the overall system may be coupled to large image data storage devices, such as a Picture Archiving and Communication System ("PACS") 44. The PACS 44 may be coupled to a remote client, as illustrated at reference numeral 46, such as for requesting and transmitting images and image data for remote viewing and processing as described herein. It should be further noted that the computer 34 and operator workstation 38 may be coupled to other output devices which may include standard or special-purpose computer monitors, computers and associated processing circuitry. One or more operator workstations 38 may be further linked in the system for outputting system parameters, requesting examinations, viewing images, and so forth. In general, displays, printers, workstations and similar devices supplied within the system may be local to the data acquisition components or remote from these components, such as elsewhere within an institution or in an entirely different location, being linked to the imaging system by any suitable network, such as the Internet, virtual private networks, local area networks, and so forth.

Figure 2:
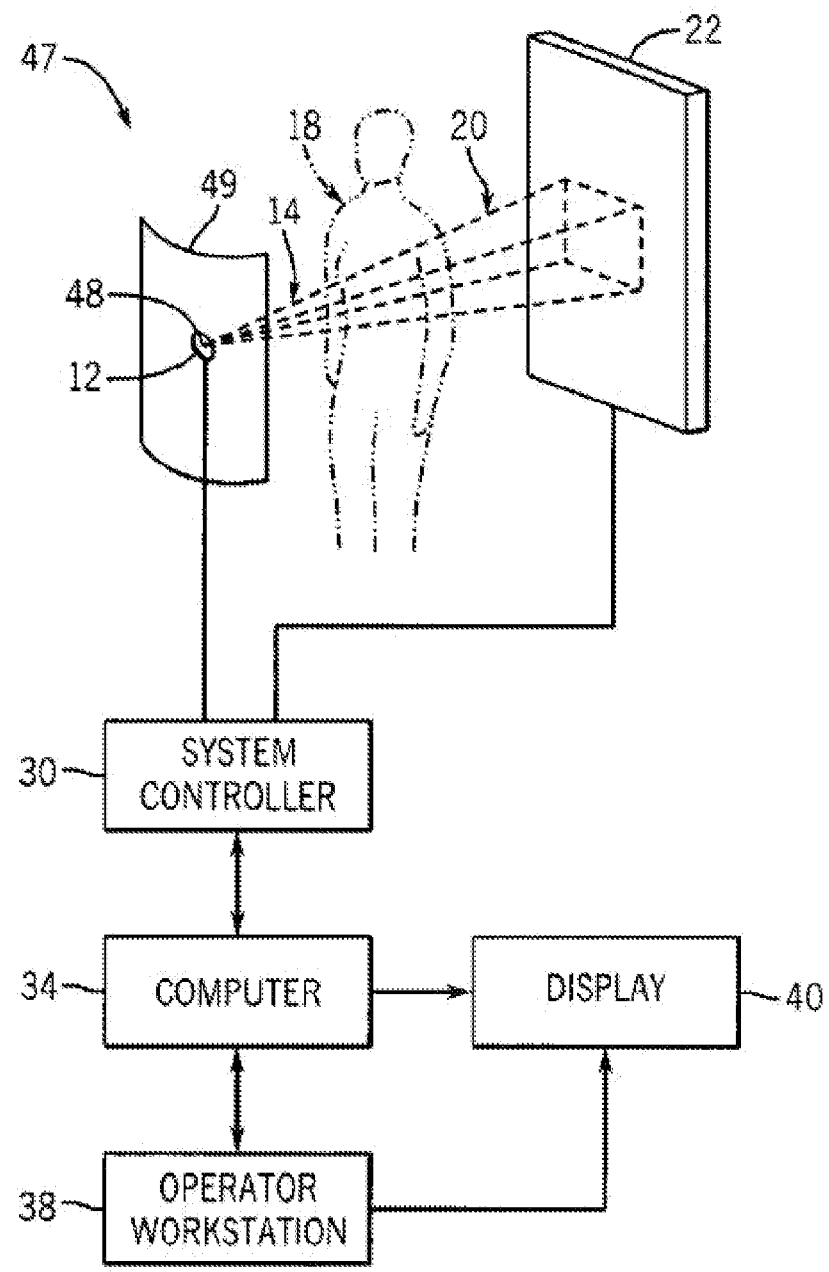
FIG. 2 is a diagrammatical view of a physical implementation of the tomosynthesis system of FIG. 1.

Referring generally to FIG. 2, an exemplary implementation of a tomosynthesis imaging system of the type discussed with respect to FIG. 1 is illustrated. Although a particular tomosynthesis imaging system is illustrated in FIG. 2, note that any other type of tomosynthesis image system, such as one associate with mammograms, may be used in accordance with any of the embodiments described herein. As shown in FIG. 2, an imaging scanner 47 generally permits interposition of a subject 18 between the source 12 and detector 22. Although a space is shown between the subject and detector 22 in FIG. 2, in some embodiments, the subject may be positioned directly before or against the imaging plane of the detector 22. For example, in digital breast tomosynthesis (DBT) the imaged breast is generally positioned directly above the detector cover. The detector 22 may, moreover, vary in size and configuration. The X-ray source 12 is illustrated as being positioned at a source location or position 48 for generating one or a series of projections. In general, the source is movable relative to the imaged anatomy such as to permit multiple such projections to be attained in an imaging sequence. In the illustration of FIG. 2, a curved source surface 49 is defined by the array of positions available to source 12. This curved source surface 49 may be representative of, for example, an X-ray tube attached to a gantry arm which rotates around a pivot point in order to acquire projections from different views. The source surface 49 may, of course, be replaced by other three-dimensional trajectories for a movable source 12. Alternatively, two-dimensional or three-dimensional layouts and configurations may be defined for multiple sources which may or may not be independently movable.

In typical operation, X-ray source 12 projects an X-ray beam from its focal point toward detector 22. A portion of the beam 14 that traverses the subject 18, results in attenuated X-rays 20 which impact detector 22. This radiation is thus attenuated or absorbed by the internal features of the subject, such as internal anatomies in the case of medical imaging. The detector 22 is formed by a plurality of detector elements generally corresponding to discrete picture elements or pixels in the resulting image data. The individual pixel electronics detect the intensity of the radiation impacting each pixel location and produce output signals representative of the radiation. In an exemplary embodiment, the detector consists of an array of 2048×2048 pixels. In another embodiment, the detector consists of an array of 2304×1920 pixels. Other detector configurations and resolutions are, of course, possible. Each detector element at each pixel location produces an analog signal representative of the impending radiation that is converted to a digital value for processing.

The source 12 is moved and triggered, or offset distributed sources are similarly triggered, to produce a plurality of projections or images from different source locations. These projections are produced at different view angles and the resulting data (i.e., the projection radiographs) is collected by the imaging system. In an exemplary embodiment involving breast imaging, the gantry or arm to which the source 12 is attached has a pivot point located at the same height as the detector 22. The distance from the focal point of the source 12 to the pivot point of the gantry or arm is 66.0 cm. The considered angular range of the gantry with respect to the pivot point is from −30 to 30 degrees, where 0 degrees corresponds to the vertical position of the gantry arm (i.e., the position where the center ray of the X-ray cone beam is perpendicular to the detector plane). With this system, typically 21 projection radiographs are acquired, each 3 degrees apart covering the full angular range of the gantry, although the number of images and their angular separation may vary. This set of projection radiographs constitutes the tomosynthesis projection dataset.

Figure 3:
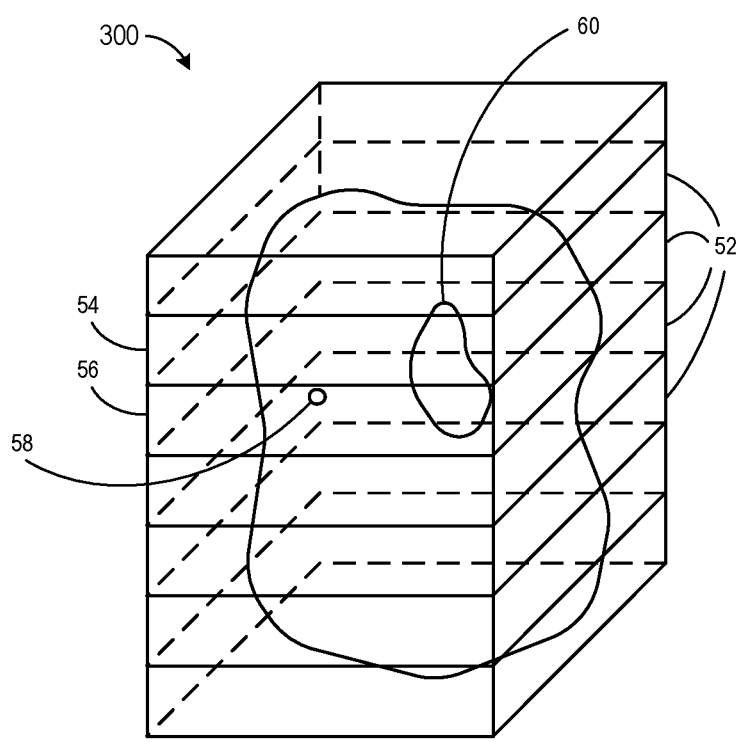
FIG. 3 is a perspective view of a three-dimensional object represented as a volume arranged in slices.

Either directly at the imaging system, or in a post-processing system, data collected by the system is manipulated to reconstruct a three-dimensional representation 300 of the volume imaged, as illustrated in FIG. 3. For example, in a process referred to as backprojection, the system performs mathematical operations designed to compute an estimate of the spatial distribution of the X-ray attenuation within the imaged object. Various reconstruction approaches to improve image quality are known in the art, including, but not limited to, filtered backprojection (where the projection images are filtered prior to being backprojected), and iterative approaches (consisting of repeated steps where the reconstructed volume may be re-projected, and compared to the original projection images, before an update to the reconstructed volume, based on backprojecting the difference between original projections and re-projected images, is generated. The reconstructed volume may be defined on a voxel grid arranged as a set of individual slices 52. Typically, in systems of the prior art, the voxel grid may have a uniform spacing between voxels within each slice, and a uniform (but maybe different) spacing between voxels in adjacent slices.

Figure 4:
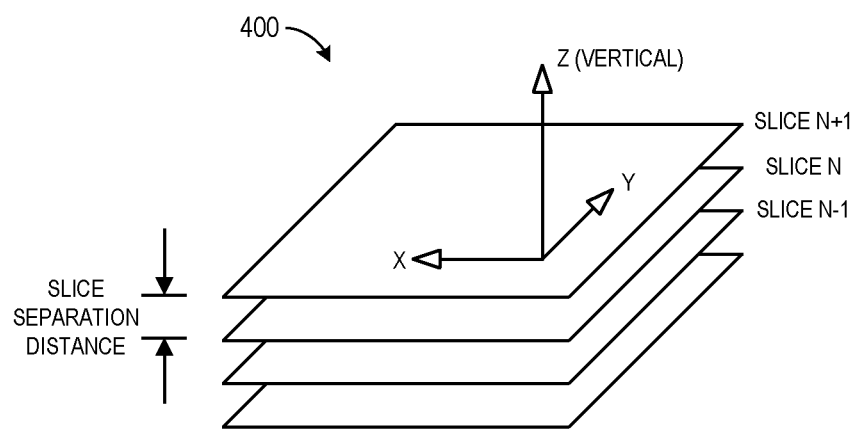
FIG. 4 illustrates a coordinate system in accordance with some embodiments described herein.

FIG. 4 is an illustration 400 of an x/y/z coordinate system that may be used to describe a volumetric image. In particular, an x/y grid may describe slices that are separated along the z axis (vertically). Note that we generally use the term "vertical" to refer to the direction of the z axis, which in turn is essentially perpendicular to the detector plane. Furthermore, in some embodiments, the detector plane may not be horizontal (or essentially horizontal). Referring again to FIG. 3, these slices 52 are generally parallel to the detector 22 plane (i.e., the x/y axes may span the detector plane), although other arrangements are possible as well. For example, a reconstructed dataset may be reformatted such that it consists of vertical slices rather than the horizontal slices 52 as illustrated in FIG. 3. In an exemplary embodiment, the spacing between slices 52 may be 1.0 mm or less. This means that, in an exemplary mammography implementation, a tomosynthesis dataset for a breast with a compressed breast thickness of 5 cm may consist of 50 or more slices 52. The voxel spacing in each slice may be about 0.1 mm, i.e., each slice has a resolution similar to a single mammogram. For a thicker breast, more slices 52 may be reconstructed. The slices 52 may be essentially stacked together to create the three-dimensional representation 300 of an imaged object.

The vertical resolution of tomosynthesis imaging may be limited by the angular range of the acquired projection images. Consider, for example, DBT volume datasets which are typically reconstructed with an anisotropic voxel size, where the in-plane voxel size usually reflects the detector pixel size (e.g., 0.1 mm), and the slice separation is generally between 0.5 and 1.0 mm. This anisotropic voxel spacing results from a combination of the limited angular range acquisition, as well as workflow (image review time) and data storage considerations. When the tomographic angle is increased, the slice spacing should be reduced; otherwise there may be a risk of losing (or degrading) fine-scale image detail (e.g., small microcalcifications). That is, in systems of the prior art, in order to preserve small structures 58 within the three-dimensional representation 50 with a high degree of accuracy, the representation 50 may be composed of many slices 52 spaced very close together. The associated large number of slices may have a detrimental effect on data image review and workflow, as well as data storage requirements.

Figure 5:
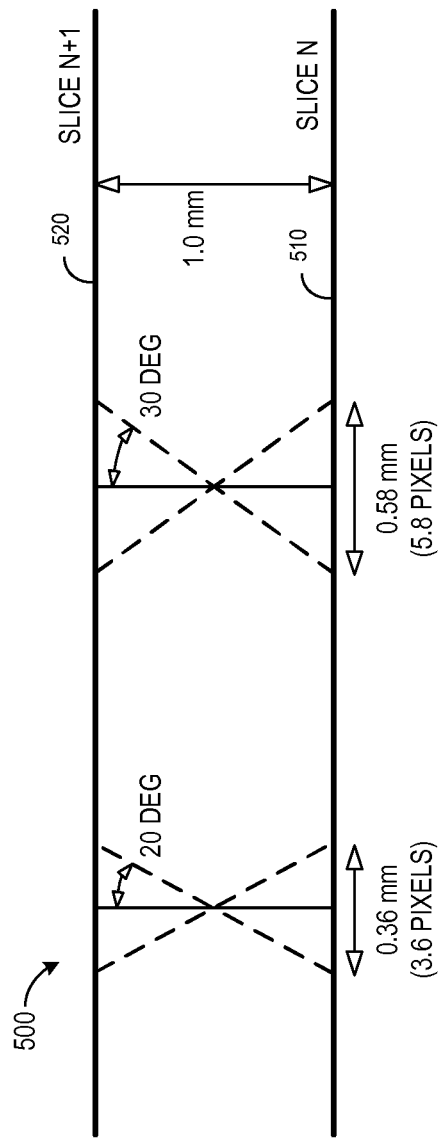
FIG. 5 illustrates blurring that may be associated with fine-detail structures located in between slices.

FIG. 5 is an illustration 500 of blurring that may be associated with fine-detail structures located in between slice N 510 and slice N+1 520. In this example 500, with a tomographic angle of ±20 degrees, a 1.0 mm slice spacing, and a 0.1 mm in-plane voxel size, a small structure located halfway between slices (i.e., offset by 0.5 mm from a nominal slice height) will suffer from a tomographic blurring (in-plane) of about ±1.8 pixels. For larger angular ranges, e.g., ±30 degrees, this blurring increases to about ±2.9 pixels. This blurring effect and the associated loss in contrast for small microcalcifications may reduce sensitivity of tomosynthesis for the detection of microcalcifications as compared to standard FFDM (full-field digital mammography). One way to address this reduction in sensitivity would be to reconstruct the volumetric image with significantly finer slice spacing in order to achieve good image quality, e.g., for small microcalcifications.

According to some embodiments described herein, a voxel grid may be adapted to the local image structure in order to reduce blurring and loss of contrast, in particular for small microcalcifications. As used herein, the term "voxel grid" may refer to a three-dimensional grid that is spatially varying, i.e., the spacing between voxels at one location within the volume is different from the voxel spacing at other locations within the volume. In one embodiment, the voxel grid is regular in-plane (i.e., in the x/y plane, parallel to the detector plane) and only the z-location of each voxel is spatially varying (i.e., the z-spacing between adjacent voxels may be different at different locations within the volume). In one embodiment, the z-location of each voxel (i.e., the voxel's vertical location or height) is adaptively adjusted within an interval around the nominal slice height.

Figure 6:
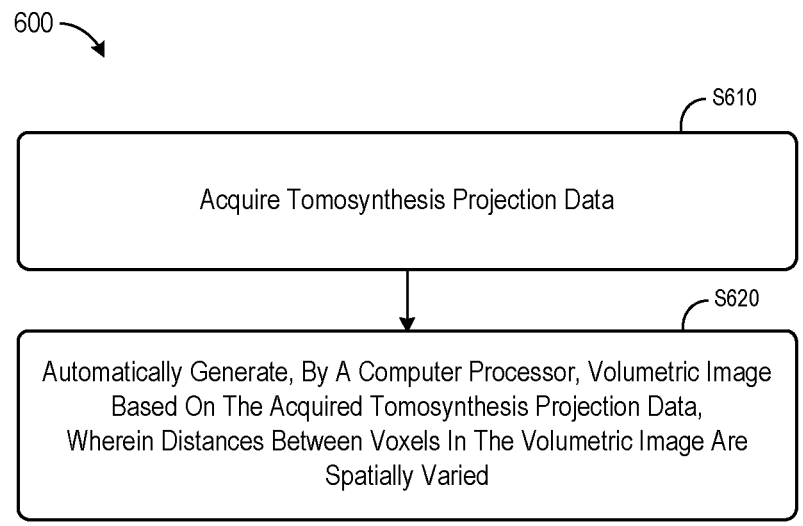
FIG. 6 is a flow chart of a method for generating a volumetric image representing an imaged object associated with a patient in accordance with some embodiments.

FIG. 6 is a flow chart of a method 600 for generating a volumetric image representing an imaged object associated with a patient in accordance with some embodiments. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At S610, tomosynthesis projection data may be acquired. The projection data may be, for example, associated with a digital breast tomosynthesis system and may be acquired in substantially real time or comprise stored data that was previously acquired. According to some embodiments, modified projection images, as discussed in more detail herein below, may be generated based on the projection data.

At S620, a volumetric image may be generated based on the acquired tomosynthesis projection data. Moreover, distances between voxels in the volumetric image may be spatially varying. Note that locations of voxels may be selected or adapted based upon information extracted from projection data. According to some embodiments, after the volumetric image is generated it may be output by storing the volumetric image in a data storage system and/or displaying the volumetric image via a display system.

According to some embodiments, the distances between voxels is "spatially varying" along a z axis and spacing between voxels in an x/y plane, substantially parallel to a detector that acquired the projection data, may be uniform. Further, for any given x/y position, there may be a fixed number of voxels distributed along the z axis and each voxel may be associated with one of a plurality of nominal slice vertical locations along the z axis. Consider, for example, FIG. 7 which is an illustration 700 of three voxels (represented as solid lines) at a particular x, y coordinate in three different slices (slices N−1, N, and N+1) according to some embodiments. Note that the selected vertical locations of the three voxels along the z axis (the location of the solid lines) differ from the associated nominal slice vertical locations (the three dashed lines).

Figure 7:
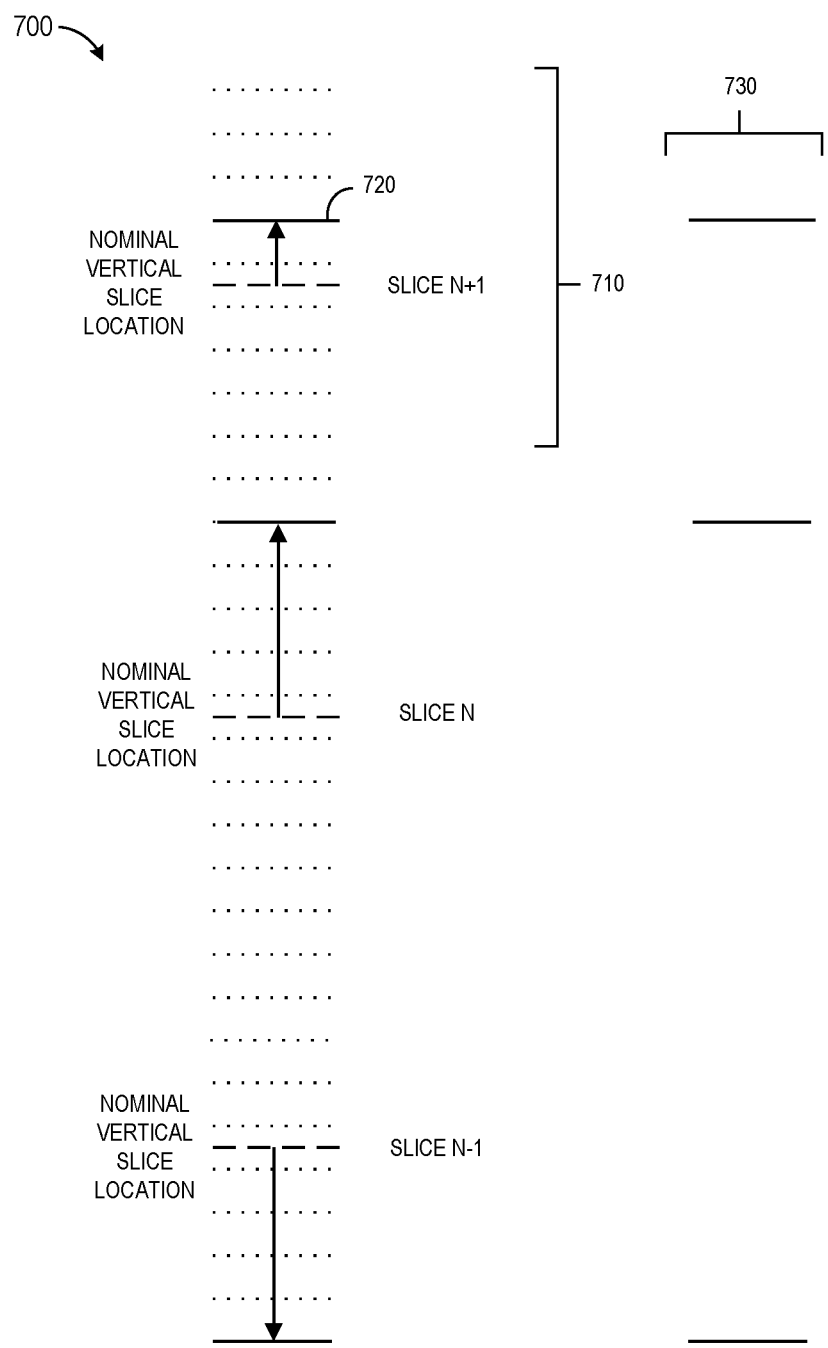
FIG. 7 illustrates, for a particular x, y coordinate, voxels at multiple slices according to some embodiments.

A difference between a nominal slice vertical location for a voxel and the selected vertical location for that voxel (depicted with arrows in FIG. 7) may be selected from a set of potential vertical adaptations 710 (e.g., represented by the five dotted lines above and the five dotted lines below the nominal vertical slice location for slice N+1). As described with respect to FIG. 10, this selection may be based on backprojected modified projection images (e.g., projection images and/or detail-only images generated from the projection images). Although only three slices are illustrated in FIG. 7, an actual volumetric image may be associated with many more slices. As seen by the representation of the three voxels standing alone 730, distances between voxels along the z axis may be spatially varied such that the distance between a first and a second voxel along the z axis is different than a distance between a second and a third voxel along the z axis.

Figure 8:
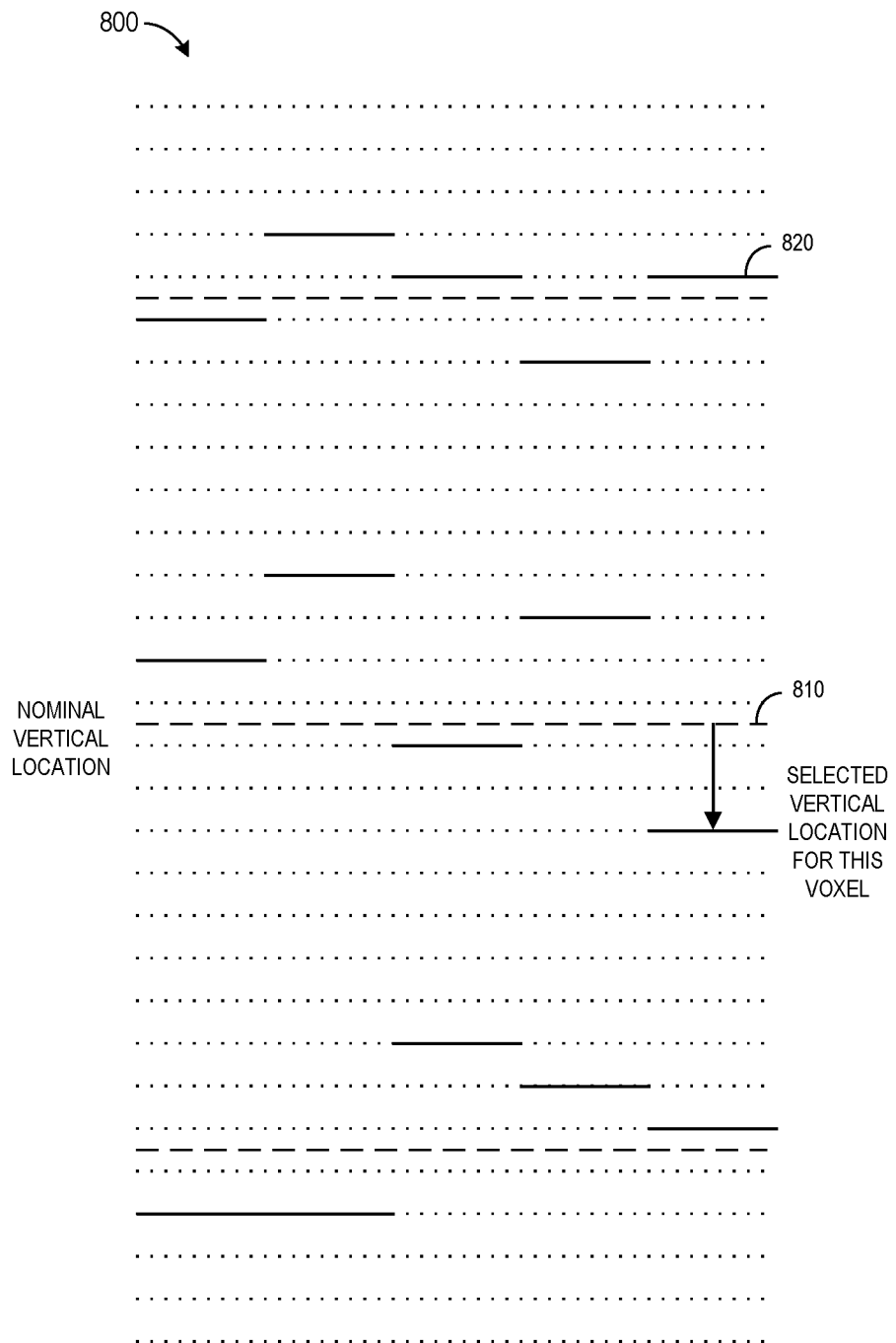
FIG. 8 is an illustration of an adaptive grid, where each voxel location is illustrated by a solid line segment, for voxels in multiple nominal slices in accordance with some embodiments.
Figure 9:
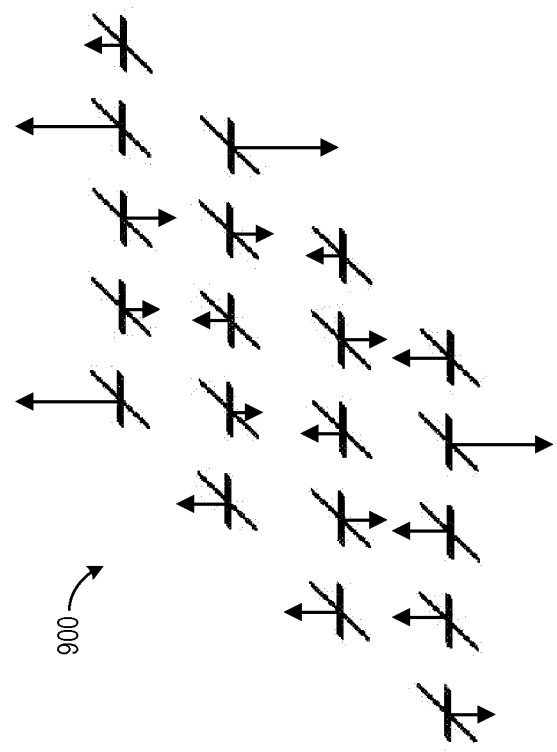
FIG. 9 illustrates voxel adaptations in a slice according to some embodiments.

FIG. 8 is an illustration of an adaptive grid 800, where each voxel location 820 may be offset from a nominal vertical location 810 as illustrated by a solid line segment in three slices in accordance with some embodiments. The in-plane pixel grid may correspond to the nominal in-plane coordinate system, while each voxel 820 has a height correction term (corresponding to the selected one of the potential vertical adaptations) that is bounded by the heights (or height intervals) of adjacent slices. Note that each slice/voxel may be considered as being "infinitesimally thin." The voxel grid 800 is in some aspects similar to a traditional voxel grid (i.e., it may be arranged in the traditional slices), but now each voxel is associated with an additional height-correction term. An advantage of this adaptive voxel grid 800 may be flexibility allowing for improved image quality. In addition, for display, image reading/review, and storage purposes the adaptive grid 800 may effectively be mapped onto the traditional grid; the only deviation from information presented on a traditional grid being the slightly different height (i.e., the fine adjustment of the z-location) associated with each voxel. In one embodiment, the height information for the voxel grid is only used during the process of reconstructing the volumetric dataset, and is not stored for later review or analysis. FIG. 9 is an illustration 900 of voxel adaptations (arrows pointing above or below the nominal voxel location represented by "+" marks) in a single slice according to some embodiments.

According to some embodiments, the height of each voxel may be determined by performing an initial reconstruction on a more finely spaced grid. Consider, for example, a nominal slice spacing of 1.0 mm, in which case the initial step may comprise a reconstruction of slices with ten times finer spacing, i.e., with a 0.1 mm separation. Then (for each voxel in every slice), a voxel height may be selected in a range around the nominal slice height as the height that "most likely" represents a microcalcification. This initial reconstruction may be, for example, based on modified projection images. In one embodiment, these modified projection images are detail-only images obtained through high-pass filtering of the acquired tomosynthesis projection images. In this case, the high-pass filtered images may be locally zero-mean (representing mostly noise and edge-like structures within the image) and microcalcifications in the images will be represented by positive (i.e., high-attenuation) values.

Figure 10:
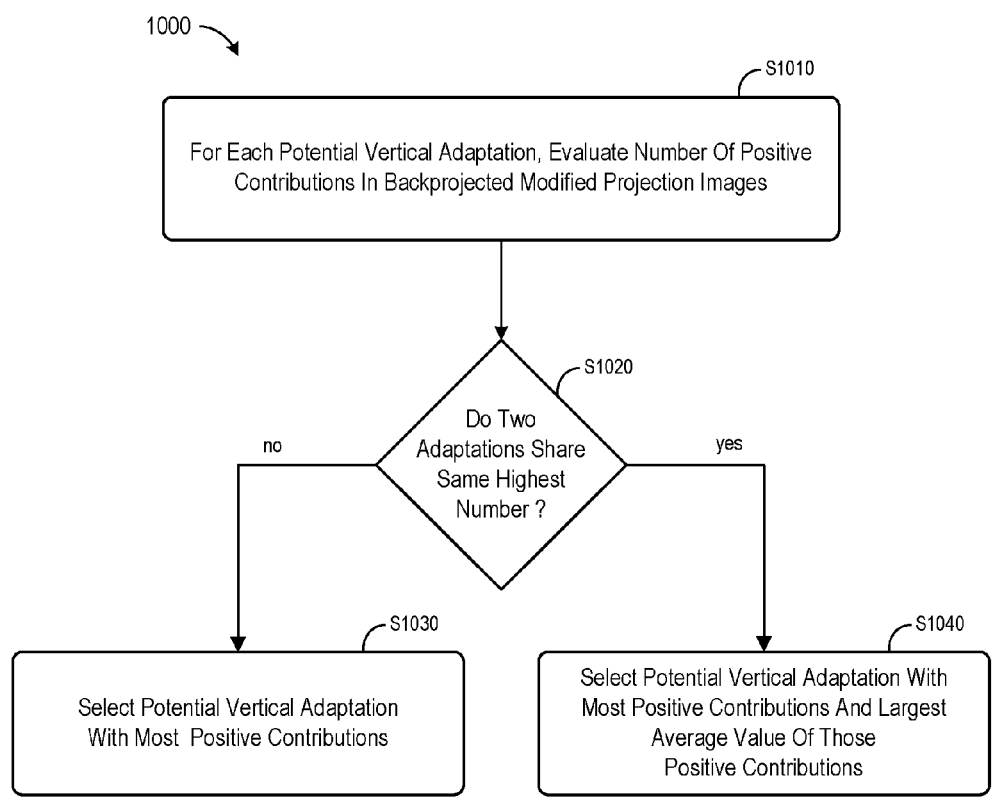
FIG. 10 is a flow chart of a method for selecting a vertical location for a voxel in accordance with some embodiments.

FIG. 10 is a flow chart of a method 1000 for selecting a vertical location for a voxel in accordance with some embodiments. At S1010, for each potential vertical adaptation, the number of positive contributions in the set of backprojected modified projection images may be evaluated. At each potential vertical adaptation, each modified projection images creates a contribution (i.e., the value determined through the back projection operation), and the set of contributions from all images is evaluated. That is, out of the set of candidate heights for each voxel the height where there is the largest number of positive contributions in the backprojection (for that height) may be selected at S1030 as the location of the voxel in the adaptive grid. This criterion may be based on an assumption that, if a microcalcification is present in this height range around the current nominal voxel location, the corresponding chosen voxel height may be an "optimal" representation of its true location in the imaged volume because the maximum number of backprojected positive values were found at that height. If there are multiple candidate voxel heights that exhibit the same (maximum) number of positive contributions at S1020, then—for this reduced set of candidate voxel heights—the height with the largest average value of those positive contributions may be selected at S1040. Other selection criteria for the selection of the vertical adaptation may be used as well.

Consider, by way of example, a reconstruction on a nominal voxel grid with a 1.0 mm slice separation. The candidate heights for each adapted voxel may range from −0.45 mm to +0.45 mm around the nominal voxel height, with 0.1 mm increments. (i.e., vertical ranges of the height adaptations of neighboring slices do not overlap, but are separated again by 0.1 mm). The optimal voxel height may be chosen from this set of considered candidate heights ("potential vertical adaptations"). Based on the adaptive voxel grid that is determined in this way, a reconstruction step may be performed to create a three dimensional reconstruction volume. Depending on the selected reconstruction algorithm, an initial estimate of the reconstructed volume may already be created as a part of the voxel grid selection step (since in this step the backprojections of the modified projection images are already computed), or the reconstruction may be performed separately using the voxel locations from the adaptive grid.

The selection of optimal voxel heights, if performed separately for each individual slice, may lead to a scenario where a microcalcification or other fine-scale structure is located approximately half-way between two adjacent slices and now both neighboring slices may attempt to claim this microcalcification as their own, by selecting the height adaptation associated with that microcalcification (in both slices). This might result in voxel adaptations that nominally belong to separate slices but are separated by only 0.1 mm or less. This "virtual duplication" of a small structure may be undesirable.

Figure 11:
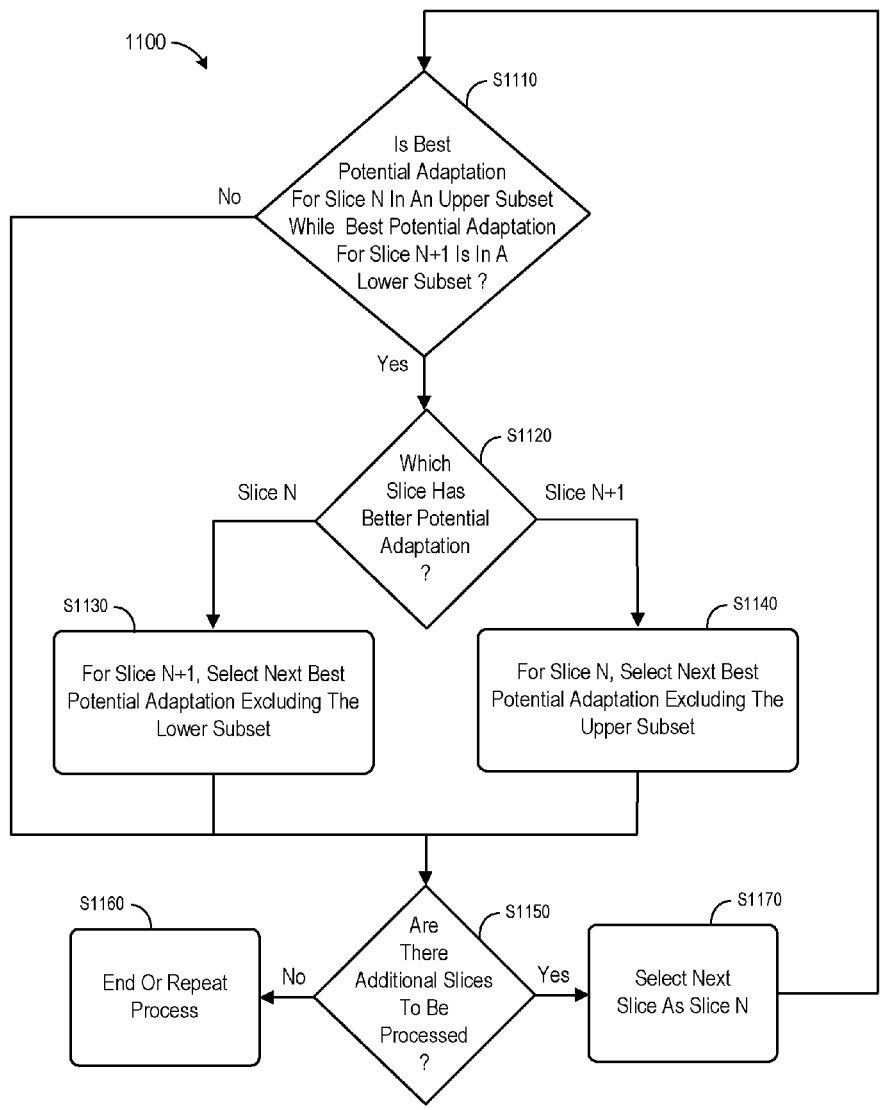
FIG. 11 is a flow chart of a method wherein a neighboring slice may influence selection of a vertical location for a voxel in accordance with some embodiments.

FIG. 11 is a flow chart of a method 1100 wherein a neighboring slice may influence selection of a vertical location for a voxel in accordance with some embodiments. That is, the selected vertical adaptation of a first voxel may be based at least in part on information associated with a second voxel at a neighboring nominal slice vertical location along the z axis. At S1110, it is determined whether: (i) the best potential adaptation for slice N is in an upper subset of potential adaptations for slice N and (ii) the best potential adaptation for slice N+1 (above neighboring slice) is in a lower subset of potential adaptations for slice N+1. For example, a set of candidate heights for each voxel may include 10 locations separated into 3 subsets: bottom or lower (3 heights or offset locations), center (4 heights), and top or upper (3 heights). If (at a single in-plane x/y location) the optimal voxel height for slice N is in the "upper" subset, while the optimal voxel height for slice N+1 is in the "lower" subset, there might be a problem if both of these best potential adaptations are selected (e.g., the selections might be too close to each other). The "best" potential adaptation within each slice might be based on, for example, the potential adaptation having the highest number of positive contributions in the backprojection and/or highest value of positive contributions. If there is no problem at S1110 the process continues at S1150.

If there is a potential problem at S1110, it is determined whether slice N or slice N+1 has the better potential adaptation at S1120. Once again, the selection of the higher quality potential adaptation might be based on a number of positive contributions and/or a value of those contributions. If slice N had the better potential adaptation, that adaptation is selected for slice N and a new potential adaptation is selected for slice N+1 at S1130. According to some embodiments, the new potential adaptation for slice N+1 is selected from the set of potential adaptations excluding the lower subset (to avoid simply repeating the same problem). That is, the new potential adaptation for slice N+1 is selected from the upper and center subsets. Similarly, if slice N+1 had the better potential adaptation, that adaptation is selected for slice N+1 and a new potential adaptation is selected for slice N at S1140, and the new potential adaptation for slice N may be selected from the set of potential adaptations excluding the upper subset (that is, the new potential adaptation for slice N is selected from the lower and center subsets).

In either case (or if no potential problem was identified at S1110), it is then determined whether there are additional slices in the volume to be processed at 1150. If there are, the next slice in the volume (i.e., slice N+1) now becomes slice N at S1170 and the process continues at S1110. If there are no additional slices to be processed at S1150 (that is, the last slice in the volume has been processed), the method may end at S1160. According to some embodiments, the entire method 1100 may instead be repeated at S1160 (e.g., all of the slices may be reprocessed). In one embodiment, when the process is the repeated, the progression is from the slice with the highest slice index to the slice with the lowest slice index, or, more generally, the order of slices is reversed when compared to the first application of the method 1100.

Using two passes of this consolidation strategy (e.g., one slice-by-slice pass for increasing slice index through the volume, followed by one pass for decreasing slice index) may generate a "balanced" adapted voxel grid, where each voxel selection is a reasonable choice with respect to the voxel height locations immediately above and below (after this consolidation step adjacent voxel heights might be at least 0.4 mm apart).

Figure 12:
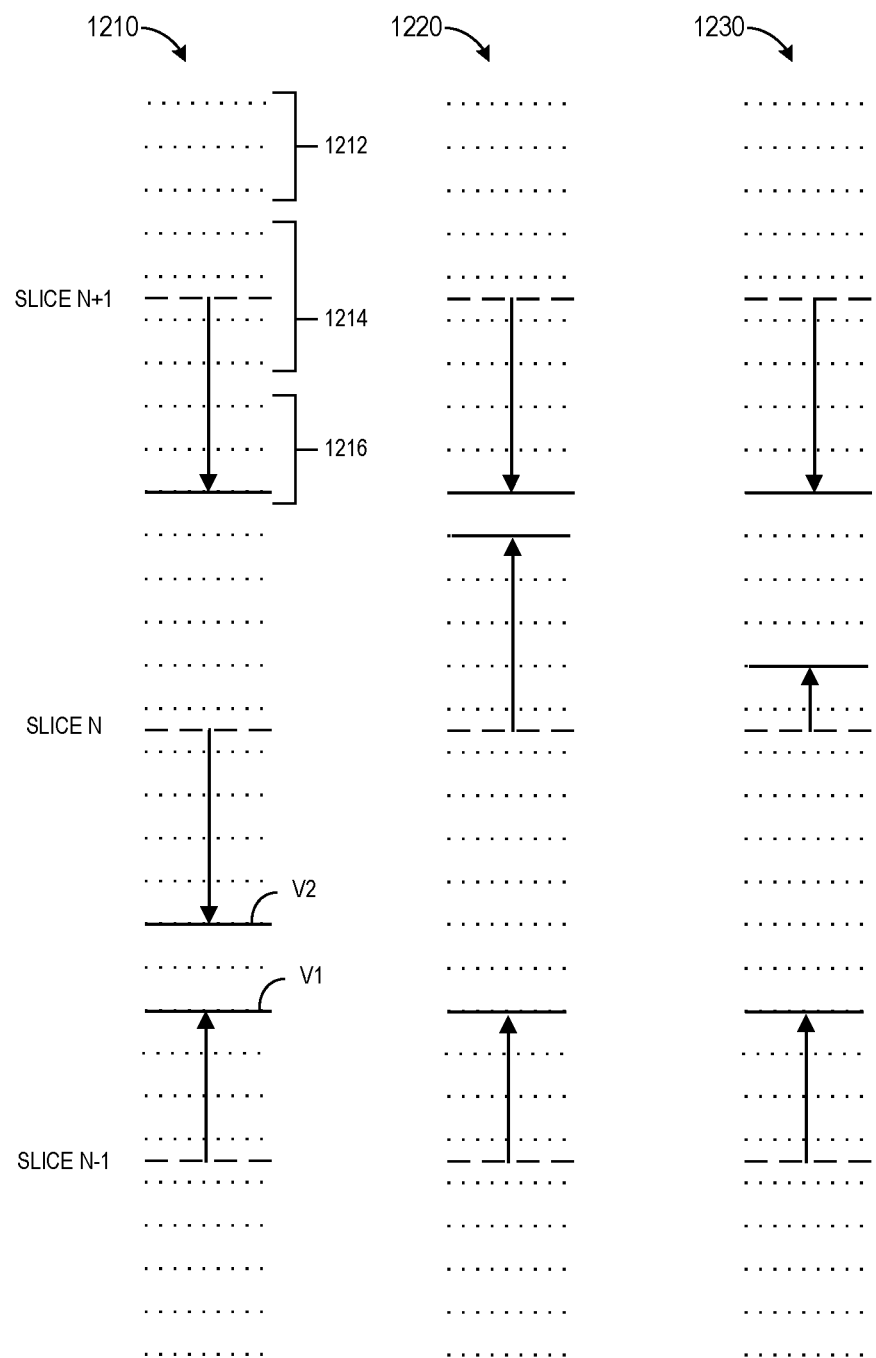
FIG. 12 is an example of how neighboring slices may influence selection of a vertical location for a voxel.

FIG. 12 is an example of how neighboring slices may influence selection of a vertical location for a voxel. In particular, selected adjusted vertical locations for a single x, y voxel position in three slices are illustrated in an initial state 1210: slice N−1, slice N, and slice N+1. Note that in slice N−1, the vertical location of voxel V1 (solid line) has been adjusted "up" four potential adjustments (dotted lined) from the nominal location (dashed line). Similarly, the vertical location of voxel V2 in slice N has been adjusted "down" five potential adjustments from the nominal location. Further note that slice N+1 illustrates three potential adjustments in a top subset 1212, four potential adjustments in a center subset 1214, and three potential adjustments in a bottom subset 1216. Similar subsets are associated with all of the slices. Note that voxel V1 is in the top subset of potential adjustments for slice N−1 and voxel V2 is in the bottom subset of potential adjustments for neighboring slice N. To avoid such a situation (because the voxels V1 and V2 are too close to each other), the method of FIG. 11 may be used to determine that voxel V1 is a better selection as compared to voxel V2. As a result, the voxel V2 in slice N may be moved as illustrated by a second state 1220 (after the initial state 1210) in FIG. 12 (where that voxel is now five potential adjustments above the nominal location).

According to some embodiments, multiple iterations or passes of this process may be performed. For example, as illustrated by the second state 1220 of FIG. 12, adjusting the vertical voxel for slice N so far above the nominal location has now created a situation where it is now too close to the selected adjustment to the voxel in slice N+1. To avoid this result, another iteration of the process may create a third state 1230 where the voxel adjustment to the vertical location for slice N has now been placed in that slice's center subset (and no vertical voxel adjustments place voxels too close to each other).

Note that this consolidation approach may require an initial reconstruction step to be performed for all heights within the reconstructed volume, such that the slice height selection criteria values are available for the full height of the reconstructed volume. Due to memory usage considerations, an algorithm may be broken down to reconstruct only a segment or sub-region in x, y at a time (in contrast to the traditional slice-by-slice ordering of a reconstruction sequence). It should also be noted that, to reduce additional blurring and contrast reduction due to the interpolation in the backprojection step, both the back—as well as the forward projection may be used with a Nearest Neighbor ("NN") interpolation.

Figure 13:
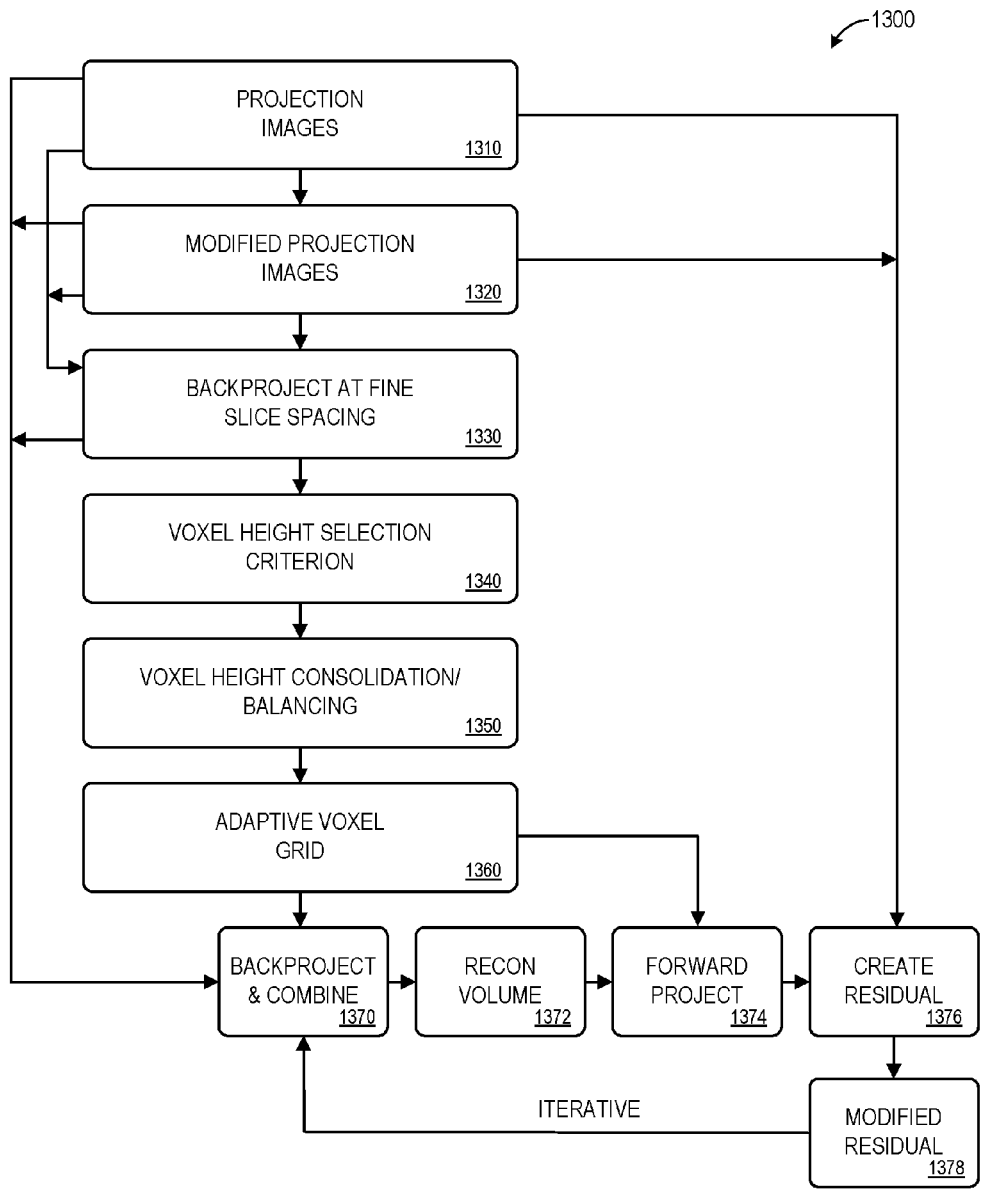
FIG. 13 illustrates a high level layout of processing elements in accordance with some embodiments.

FIG. 13 illustrates a high level layout 1300 of processing elements in accordance with some embodiments. A set of projection images 1310 may be used to create modified projection images 1320 which, in turn, may be used (along with the projection images 131) for backprojections at fine slice spacing 1330. Voxel height criterion 1340 may be processed (for example, as described with respect to FIG. 10). Voxel height consolidation and/or balancing 1350 may also be performed (for example, as described with respect to FIGS. 11 and/or 12) to generate an adaptive voxel grid 1360. The projection images 1310, modified projection images 1320, backprojections at fine spacing 1330, and/or the adaptive voxel grid 1360 may then be stored, processed (e.g., used in a reconstruction process, generating a reconstructed volume 1372), and/or output.

For example, the adaptive voxel grid 1370 may be used (as representing the voxel locations) in backprojections and combination of data 1370 (which may also include appropriately filtered projection images—not shown in Figure), thereby creating an (initial) reconstructed volume 1372. In an iterative reconstruction process, this may be followed by forward projections 1374. Residual information may be created 1376 (relative to the original projection images 1310 and/or modified projection images 1320), e.g., by subtracting the re-projected data from those images. The residual images may then be modified 1378 (e.g., appropriately filtered) in an iterative process to create an updated and/or final tomographic volumetric image representing an imaged object associated with a patient.

FIG. 14 is an example of results 1400 that may be achieved according to some embodiments described herein. The results 1400 might be associated with, for example, 21 projection views, separated by 3 degrees, for a total angular range of ±30 degrees. The adaptive voxel grid may be provided in accordance with any of the embodiments described herein, and both the reconstruction of the fine-scale detail (used in the derivation of the adaptive grid) as well as a subsequent Generalized Filtered Backprojection ("GFBP") reconstruction may be performed. As used herein, the term "GFBP" may refer to a scale-enhancing filtering (mimicking a modified ramp-filter, implemented as a multi-scale decomposition followed by a recombination of appropriately weighted image scales) followed by simple back-projection on the adaptive voxel grid.

A first drawing 1410 comprises reconstruction of fine-scale information using a nominal grid having a slice spacing of 1.0 mm. In the first drawing 1410, a large structure 1412 can be seen. A second drawing 1420 comprises reconstruction using an adaptive grid that allows for voxel specific height-correction terms within the interval from −0.45 mm to +0.45 mm with 0.1 mm increments. As can be seen, the second drawing 1420 includes both a large structure 1422 and a smaller structure 1424, such as a 50 micron microcalcification that was not visible without use of the adaptive grid.

Thus, some embodiments may provide improved image quality, in particular for small microcalcifications, including improved contrast and reduced artifacts. In conjunction with other reconstruction methods, e.g., iterative methods, reduced data volume may be achieved (two times or more) for display/review and storage along with faster reconstruction times (in comparison to an iterative process on a finer grid), since the reconstruction may act on the adaptive grid only once it has been determined (before, or as part of, the first iteration). Note that embodiments may be combined with other approaches for reduction of artifacts (e.g., iterative weighted backprojection, and order statistics-based backprojection (OSBP)).

Although specific embodiments have been described herein, embodiments may, for example, be associated with any representation of volumetric reconstruction data on an adaptive grid. For example, a grid may be regular in the x/y plane (i.e., "in-plane," parallel to detector plane) and the height of the grid for each slice may vary around a "nominal" grid height on a fixed sub-grid along the z axis, where each pixel in a given slice is associated with one "dh" (delta in height relative to a nominal slice location, i.e., a height correction term). In this case, each slice may be collapsed onto the nominal grid for display/review/storage purposes. In some case an adaptive grid height may be selected in first reconstruction step (backprojection) as follows: reconstruct image detail on a finer grid (in z); for each nominal slice height (and for each pixel in slice) select dh (by selecting from a set of potential height adaptations) as function of, for example, a number of backprojected values that indicate positive detail (due to the potential presence of a microcalcification), or maximize backprojected value at that location, or a hybrid version, or any other appropriate criterion.

In some embodiments, the system may default to the nominal height when a minimum criterion is not satisfied (e.g., a minimum threshold number of pixels might be needed to indicate that a high-contrast structure is present). In some embodiments, the adaptive grid may default to the nominal slice heights in all of the reconstructed volume with the exception of a few selected regions. In one embodiment these selected regions may be selected with the help of an operator. In other embodiments, regions may be automatically selected, based on classification of image content. For example, in one embodiment the regions that are selected are the regions containing tissue (as opposed to air/background). In another embodiment, the regions may be selected as a function of the percent glandular content (i.e., regions with more than 50% glandular tissue content). In some cases, approaches for artifact management, such as Order Statistics-Based Backprojection ("OSBP") and/or weighted backprojection may be utilized. Note that the system may iterate on reconstruction of fine scale detail, but the adaptive slice height might not be updated after an initial step. In other cases, an adapted slice height may be updated in a later iteration step after the initial step. In one embodiment, the backprojected detail-only images may be used to create an initial detail-only reconstruction volume, and an iterative reconstruction process builds on that initial volume.

During an iteration, residual and re-computed detail images may be created (now based on residual) after each iteration or the same detail images may be used. Some embodiments may use NN interpolation in reconstruction (backprojection, forward projection) to minimize reduction of contrast of small microcalcifications due to interpolation inherent in projection (back and forward) operators. A pyramidal "nominal" coordinate system may be used according to some embodiments to minimize mismatch (i.e., number of voxels that are either missed or visited multiple times in NN interpolation scheme) in NN projection and back-projection. In a pyramidal coordinate system an average magnification factor may be assigned to each slice (i.e., average magnification for that slice based on all projection angles), and the in-plane voxel separation for that slice may be chosen to be the pixel separation in the detector divided by that magnification factor for that slice. In this way, the in-plane voxel separation (which is uniform within each slice) decreases with increasing height of the slice above the detector. Adapted voxel heights may now be selected relative to this nominal voxel grid. In some embodiments the reconstruction algorithm may combine detail reconstruction (containing microcalcifications) with reconstruction of background, filtered backprojection, iterative updates, and/or any combination thereof.

Note that the reconstruction of a background image (which may not contain any fine-scale detail) may be performed on the nominal grid (as opposed to the adapted grid). Moreover, a detail image (e.g., a set of modified projection images) for the construction of the adaptive voxel grid (and the reconstruction of microcalcifications) may be derived by subtracting a low-pass filtered version of projection images from the original images; or may instead be derived as residual after an initial reconstruction of mid- to coarse-scale background on the nominal grid (or a hybrid/combination approach may be used). Similarly, mid- or coarse-scale images for the reconstruction of the "background" may be derived by image filtering; as the residual after reconstruction of fine scale detail, or combination thereof.

Low-pass filtered version of projection images may be derived, e.g., by using symmetric/isotropic (two dimensional) filters (e.g., Gaussian kernel); asymmetric filters (preferential smoothing in direction of tomosynthesis scan, or even a one dimensional filter); anisotropic diffusion; or any other technique.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for generating a volumetric image representing an imaged object associated with a patient, comprising:
    acquiring tomosynthesis projection data; and
    automatically generating, by a computer processor, the volumetric image based on the acquired tomosynthesis projection data, wherein distances between voxels in the volumetric image are spatially varied;
    wherein the distances between voxels is spatially varied along a z axis and spacing between voxels in an x/y plane, substantially parallel to a detector that acquired the projection data, is uniform.

2. The method of claim 1, wherein locations of one or more voxels are selected based upon information extracted from projection data.

3. The method of claim 1, wherein, for any given x/y position, there are a fixed number of voxels distributed along the z axis.

4. The method of claim 3, wherein each voxel is associated with one of a plurality of nominal slice vertical locations along the z axis.

5. The method of claim 4, wherein selected vertical locations of one or more voxels along the z axis differ from the associated nominal slice vertical locations.

6. The method of claim 5, wherein a difference between a nominal slice vertical location for a voxel and the selected vertical location for that voxel is selected from a set of potential vertical adaptations.

7. The method of claim 6, wherein the selection is based upon backprojected modified projection images.

8. The method of claim 7, wherein the modified projection images comprise at least one of: (i) projection images, and (ii) detail-only images generated from the projection images.

9. The method of claim 8, wherein said selection comprises evaluating numbers of positive contributions in the backprojected modified projection images at each of the set of potential vertical adaptions.

10. The method of claim 5, wherein the selected vertical adaptation of a first voxel is based at least in part on information associated with a second voxel at a neighboring nominal slice vertical location along the z axis.

11. The method of claim 1, wherein said acquiring of the tomosynthesis projection data comprises one of: (i) acquiring the data in substantially real time, or (ii) retrieving stored data that was previously acquired.

12. The method of claim 1, wherein distances between voxels is spatially varied such that the distance between a first and a second voxel is different than a distance between the second and a third voxel along at least one axis.

13. The method of claim 1, further comprising:
    outputting the volumetric image by performing at least one of: (i) storing the volumetric image in a data storage system, or (ii) displaying the volumetric image via a display system.

14. The method of claim 1, wherein the acquired tomosynthesis projection data is associated with a digital breast tomosynthesis dataset.

15. A non-transitory, computer-readable medium storing instructions that, when executed by a computer processor, cause the computer processor to perform a method for generating a volumetric image representing an imaged object associated with a patient, the method comprising:
    acquiring tomosynthesis projection data; and
    generating the volumetric image based on the acquired tomosynthesis projection data, wherein distances between voxels in the volumetric image are spatially varied;
    wherein the distances between voxels is spatially varied along a z axis and spacing between voxels in an x/y plane, substantially parallel to a detector that acquired the projection data, is uniform.

16. The medium of claim 15, wherein locations of one or more voxels are selected based upon information extracted from projection data.

17. The medium of claim 15, wherein, for any given x/y position, there are a fixed number of voxels distributed along the z axis.

18. A system for generating a volumetric image representing an imaged object associated with a patient, comprising:
    an input port to acquire tomosynthesis projection data; and
    a computer system coupled to the input port to generate the volumetric image based on the acquired tomosynthesis projection data, wherein distances between voxels in the volumetric image are spatially varied;
    wherein the distances between voxels is spatially varied along a z axis and spacing between voxels in an x/y plane, substantially parallel to a detector that acquired the projection data, is uniform.

19. The system of claim 18, wherein locations of one or more voxels are selected based upon information extracted from projection data.

20. The system of claim 18, wherein, for any given x/y position, there are a fixed number of voxels distributed along the z axis.

* * * * *

UNITED STATES PATENT AND TRADEMARK OFFICE
CERTIFICATE OF CORRECTION

| | | |
|---|---|---|
| PATENT NO. | : 9,613,440 B2 | Page 1 of 2 |
| APPLICATION NO. | : 14/178702 | |
| DATED | : April 4, 2017 | |
| INVENTOR(S) | : Claus | |

It is certified that error appears in the above-identified patent and that said Letters Patent is hereby corrected as shown below:

On the Title Page

In Item (56), under "U.S. PATENT DOCUMENTS", in Column 2, Line 6, delete "Claus" and insert -- Claus et al. --, therefor.

On Page 2, in Item (56), under "U.S. PATENT DOCUMENTS", in Column 1, Line 1, delete "Ren" and insert -- Ren et al. --, therefor.

On Page 2, in Item (56), under "U.S. PATENT DOCUMENTS", in Column 1, Line 3, delete "Fischer" and insert -- Fischer et al. --, therefor.

On Page 2, in Item (56), under "U.S. PATENT DOCUMENTS", in Column 1, Line 5, delete "Ruth" and insert -- Ruth et al. --, therefor.

In the Drawings

In Fig. 2, Sheet 2 of 14, delete Tag "30" and insert Tag -- 24 --, therefor.

In the Specification

In Column 1, below Title, insert -- STATEMENT REGARDING FEDERALLY SPONSORED RESEARCH OR DEVELOPMENT
This invention was made with Government support under award number R01CA151443 awarded by the National Institutes of Health through the National Institute of Biomedical Imaging and Bioengineering. The Government has certain rights in this invention. --.

In Column 4, Line 37, delete "associate" and insert -- associated --, therefor.

In Column 5, Line 46, delete "(consisting" and insert -- consisting --, therefor.

Signed and Sealed this
Thirtieth Day of May, 2017

Michelle K. Lee
*Director of the United States Patent and Trademark Office*

In Column 8, Line 66, delete "increments." and insert -- increments, --, therefor.

In Column 11, Line 19, delete "voxel grid 1370" and insert -- voxel grid 1360 --, therefor.

In Column 11, Lines 56-57, delete "50 micron" and insert -- 50 microns --, therefor.

In Column 12, Line 61, delete "system" and insert -- system, --, therefor.

In Column 13, Line 3, delete "embodiments" and insert -- embodiments, --, therefor.

In the Claims

In Column 14, Line 35, in Claim 15, delete "non-transitory," and insert -- non-transitory --, therefor.

In Column 14, Line 49, in Claim 16, delete "medium" and insert -- non-transitory computer-readable medium --, therefor.

In Column 14, Line 52, in Claim 17, delete "medium" and insert -- non-transitory computer-readable medium --, therefor.